United States Patent [19]

Belle

[11] 4,223,018

[45] Sep. 16, 1980

[54] BATH COMPOSITION

[76] Inventor: Jimmie Belle, 1900 Main St. #5, Boise, Id. 83706

[21] Appl. No.: 10,998

[22] Filed: Feb. 9, 1979

[51] Int. Cl.$^2$ ................ A61K 31/595; A61K 31/365; A61K 35/78; A61K 37/00

[52] U.S. Cl. .................................. 424/177; 424/195; 424/237; 424/280; 424/359

[58] Field of Search ................ 424/359, 70, 127, 237, 424/280, 195, 177

[56] References Cited

U.S. PATENT DOCUMENTS

| | | | |
|---|---|---|---|
| 2,865,859 | 12/1958 | Lubowe | 424/66 |
| 2,876,164 | 3/1959 | Wershaw | 424/359 |
| 3,340,153 | 9/1967 | Kart | 424/359 |
| 3,463,862 | 8/1969 | Mazza | 424/359 |
| 3,622,668 | 11/1971 | Moss | 424/346 |
| 3,810,996 | 5/1974 | Sutliff et al. | 424/359 |
| 4,005,210 | 1/1977 | Gubenwick | 424/359 |
| 4,076,800 | 2/1978 | Marsh et al. | 424/359 |

FOREIGN PATENT DOCUMENTS 50-155637  12/1975  Japan ........................................ 424/359

OTHER PUBLICATIONS

Cosmetics-Sci and Tech.-Sarparin, Interscience Pub. Inc., N.Y., (1957), pp. 107, 160–161.

Am. Perf. & Cos., vol. 81 (12) 1966, pp. 43–50, Goldrick.

Am. Perf. & Cos., vol. 82, (1967), pp. 47–48, 55–57, Cotte et al.

*Primary Examiner*—Douglas W. Robinson
*Attorney, Agent, or Firm*—Larson, Taylor and Hinds

[57] ABSTRACT

A bath composition which is added to a user's bath water comprising hydrochloric acid, ascorbic acid, protein powder, olive oil, vitamin $D_2$ and vitamin A is found to cleanse the skin and restore vitamins and protein thereto.

1 Claim, No Drawings

BATH COMPOSITION

FIELD OF THE INVENTION

This invention relates generally to bath compositions and more particularly to a composition which cleanses the body using a solution which contains vitamins, protein and oils.

BACKGROUND OF THE INVENTION

Many solutions of differing compositions which are designed to be applied to the skin are known in the prior art. An example of a medicinal compound which includes vitamins A and D and olive oil is disclosed in U.S. Pat. No. 3,622,668 to Moss. A cosmetic oil also including vitamins A and D and olive oil is disclosed in U.S. Pat. No. 2,865,859 to Lubowe.

It has also been disclosed in U.S. Pat. No. 2,876,164 to Wershaw to combine protein, acid and vitamins to form a dermotological preparation for topical application to the skin. The acid in this composition is used to adjust the pH of the preparation to that of normal skin.

However, none of the foregoing prior art compositions has provided a cleansing composition which cleans the body and at the same time restores essential vitamins and proteins to the body through the skin. These absorbed proteins and vitamins act to promote healing of lacerations as well as general body health.

SUMMARY OF THE INVENTION

The present invention provides a novel bath composition which is added to a user's bath water, for cleansing the skin. The present invention restores vitamins and proteins to the body when it contacts the skin.

An object of the invention is to provide a bath composition which contains vitamins and proteins. Such a composition helps promote healing of lacerations and general body health.

The bath composition comprising this invention contains the following: hydrochloric acid, ascorbic acid, protein powder, olive oil, vitamin $D_2$ and vitamin A. The proportions which the bath compositions contain are the following: about 0.048 to 0.049 percent by weight of 6 M hydrochloric acid; about 1.085 to 1.107 percent by weight of ascobic acid; about 19.215 to 19.603 percent by weight of protein powder; about 76.832 to 78.384 percent by weight of olive oil; about 1.097 to 1.118 percent by weight of vitamin $D_2$ in propylene glycol; and about 0.723 to 0.738 percent by weight of vitamin A in sulfurized castor oil.

Other features, objects and advantages of the present invention are stated in or apparent from the detailed description of a presently preferred embodiment of the invention found hereinbelow.

DETAILED DESCRIPTION OF THE PREFERRED EMBODIMENT

The preparation of one dosage of this bath composition, approximately 6.788 c.c. or 6.842 grams, using commercially available products is accomplished in the following manner. Starting with 12 M HCl, such as that manufactured by The J. T. Baker Chemical Company, this is diluted with an equal portion of distilled water to obtain 6 M HCl. This mixing will produce heat and is left standing till it reaches room temperature. About 3.30 mgm of this 6 M HCl at room temperature is then mixed with 5310.0 mgm of olive oil. This olive oil should be pure olive oil which is free from foreign matter. A suitable olive oil is manufactured by Pompeian, Inc. under the name "Pompeian Olive Oil". it is important that the HCl be mixed with the olive oil before any other ingredients are added, otherwise the HCl will react chemically with the other ingredients and ruin the preparation.

After mixing the HCl and olive oil completely, the ascorbic acid is added. A convenient form of ascorbic acid is an ascorbic acid powder manufactured by BBC Laboratories. In the form produced by BBC Laboratories, 75.0 mgm should be added to the solution.

Once the ascorbic acid is thoroughly mixed, the protein powder is added. It is important that the protein powder be added at this stage because at this point it does not react with any of the other ingredients. An excellent protein powder for this purpose is manufactured by the Vitamix Co. and it contains the following: calcium caseinate, lactalbumin, non fat dry milk, soy protein isolate, defatted whole egg powder, and lecithin. This product is at least 76% protein. In such a form, 1328.0 mgm is added to the solution and mixed in thoroughly.

The next ingredient which is added is the vitamin $D_2$. A liquid form of vitamin $D_2$ made by Winthrop Laboratories is convenient for this purpose, as it will readily dissolve in the solution. The product is called "Dristol in propylene glycol" and contains 8000 units of ergocalciferol per gram. Using this product, 75.75 mgm is added slowly and thoroughly mixed into the solution.

The last ingredient added to the solution is vitamin A. A liquid form of this vitamin is also convenient and a product called "Aquasol A Drops Aqueous Vitamin A" manufactured by the U.S.V. Pharmaceutical Corp. has been found to mix satisfactorily with the solution. The "Aquasol A" contains 5.000 U.S.P. units per c.c. in sulphurized castor oil, and 50.0 mgm of this product is added and mixed in the solution.

The ascorbic acid must be dissolved thoroughly into the solution and it may be convenient to let the mixture sit overnight to accomplish this.

The resulting solution weighs approximately 6,842 mgm or 6.842 grams, has a pH of 4.5 and a density of 1.008 gm/ml. For use, the solution is conveniently dispensed from an individual-portion non-reactive container of polypropalene. A suitable container is made by Evergreen Scientific, model No. 3010H. A box or such, should be used to protect the containers from sunlight, etc.

The following example illustrates a specific formulation that may be employed for the bath composition of the present invention.

EXAMPLE

6 M HCl: 3.30 mgm;
Olive Oil: 5310.0 mgm;
Ascorbic Acid: 75.0 mgm
Protein Powder: 1328.0 mgm;
"Dristol in Propylene Glycol" (Vitamin D): 75.75 mgm;
"Aquasol A" (Vitamin A): 50.0 mgm;

The use of the solution as a bath composition is much the same as a bath oil. After filling the bathtub with water, one dosage of the bath composition (6.842 grams) is added. Once the solution is in the bath water, the bath water is stirred to mix the solution in the water. The bather then enters the water and soaks for a minute or longer on his front side and a minute or longer on his back side, immersing his ears to allow water to enter. After both sides have soaked thoroughly, the bather uses a wash cloth to scrub his body clean using plenty of bath water. Hair is cleaned by brushing with a stiff brush using bath water until it is clean, soft, and shiny. The bath composition of this invention should not be used with any other bath preparations or soap, or reused by another person. As the dirt and dead skin cells are washed from the body, the skin absorbs some of the vitamins and proteins which are in the bath water, promoting healing of lacerations and general body health.

Although the invention has been described in detail with respect to exemplary embodiments thereof, it will be understood by those of ordinary skill in the art that variations and modifications may be effected within the scope and spirit of the invention.

I claim:

1. A bath composition which is added to a user's bath water comprising:
   about 0.048 to 0.049 percent by weight of 6 M hydrochloric acid;
   about 1.08 to 1.11 percent by weight of ascorbic acid;
   about 19.22 to 19.60 percent by weight of protein in powder form consisting essentially of calcium caseinate, lactalbumin, non-fat dry milk, soy protein isolate, defatted whole egg powder, and lecithin where the protein makes up about 76–79 percent of the powder;
   about 76.83 to 78.38 percent by weight of olive oil;
   about 1.10 to 1.12 percent by weight of vitamin $D_2$ in propylene glycol; and
   about 0.72 to 0.74 percent by weight of vitamin A in sulfurized castor oil.